(12) United States Patent
Nickel et al.

(10) Patent No.: US 12,313,556 B2
(45) Date of Patent: May 27, 2025

(54) OPTICAL INTERFERENCE DIAGNOSTIC APPARATUS AND METHODS OF USE

(71) Applicant: PAVONIS DIAGNOSTICS INC., Edmonton (CA)

(72) Inventors: Matthew R. Nickel, Leduc (CA); Hillary M. Sweet, Leduc (CA)

(73) Assignee: PAVONIS DIAGNOSTICS INC., Edmonton (CA)

( * ) Notice: Subject to any disclaimer, the term of this patent is extended or adjusted under 35 U.S.C. 154(b) by 1036 days.

(21) Appl. No.: 17/285,819

(22) PCT Filed: Dec. 16, 2020

(86) PCT No.: PCT/CA2020/051730
§ 371 (c)(1),
(2) Date: Apr. 15, 2021

(87) PCT Pub. No.: WO2021/119814
PCT Pub. Date: Jun. 24, 2021

(65) Prior Publication Data
US 2022/0128479 A1    Apr. 28, 2022

Related U.S. Application Data

(60) Provisional application No. 62/951,560, filed on Dec. 20, 2019.

(51) Int. Cl.
| | | |
|---|---|---|
| G01N 21/78 | (2006.01) |
| A61B 5/00 | (2006.01) |
| C25D 11/02 | (2006.01) |
| C25D 11/08 | (2006.01) |
| C25D 11/10 | (2006.01) |
| C25D 11/22 | (2006.01) |
| G01N 21/45 | (2006.01) |

(52) U.S. Cl.
CPC .......... G01N 21/78 (2013.01); A61B 5/0059 (2013.01); C25D 11/022 (2013.01); C25D 11/08 (2013.01); C25D 11/10 (2013.01); C25D 11/22 (2013.01); G01N 21/45 (2013.01)

(58) Field of Classification Search
CPC ......... A61B 5/0059; G01N 2021/7773; G01N 21/45; G01N 21/78; G01N 21/8422; C25D 11/22; C25D 11/022; C25D 11/08; C25D 11/10
See application file for complete search history.

(56) References Cited

U.S. PATENT DOCUMENTS 3,979,184 A    9/1976   Giaver
4,066,816 A    1/1978   Sheasby et al.
(Continued)

OTHER PUBLICATIONS

International Preliminary Report on Patentability for International (PCT) Patent Application No. PCT/CA2020/051730, dated Jun. 30, 2022, 7 pages.
(Continued)

*Primary Examiner* — Kathryn Elizabeth Limbaugh
(74) *Attorney, Agent, or Firm* — Sheridan Ross P.C.

(57) ABSTRACT

An improved thin film optical interference apparatus, methods of use and of manufacture are provided, the apparatus comprising means for generating optical interference colours directly on the surface of a single layer of anodized metal. The interference colours generated by the presently improved apparatus can be used to indicate the presence of at least one organic compound or analyte.

24 Claims, 6 Drawing Sheets

(56) References Cited

U.S. PATENT DOCUMENTS

| | | |
|---|---|---|
| 4,310,586 A | 1/1982 | Sheasby et al. |
| 4,558,012 A | 12/1985 | Nygren et al. |
| 5,112,449 A | 5/1992 | Jozefowicz et al. |
| 5,124,172 A | 6/1992 | Burrell et al. |
| 5,167,793 A | 12/1992 | Jozefowicz |
| 5,218,472 A | 6/1993 | Jozefowicz et al. |
| 5,468,606 A | 11/1995 | Bogart et al. |

OTHER PUBLICATIONS

International Search Report and Written Opinion for International (PCT) Patent Application No. PCT/CA2020/051730, dated Jan. 25, 2021.

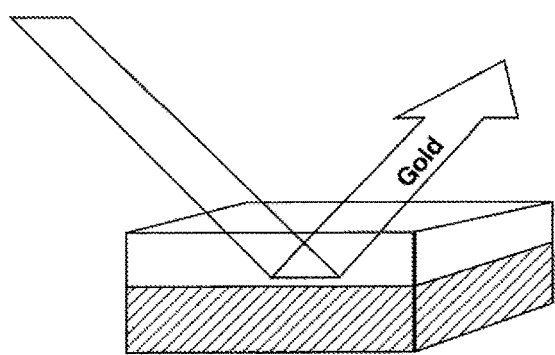
FIGURE 1A
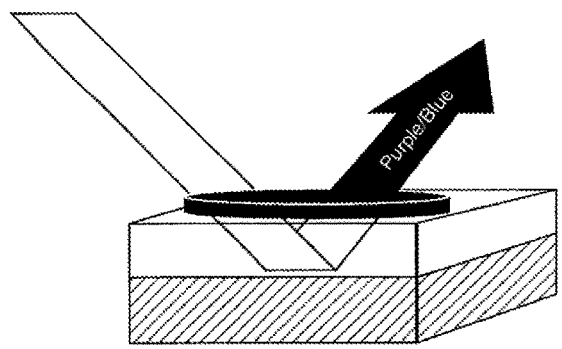
FIGURE 1B
*FIG. 1*
*(PRIOR ART)*

OPTICAL INTERFERENCE DIAGNOSTIC APPARATUS AND METHODS OF USE

CROSS REFERENCE TO RELATED APPLICATIONS

This application is a national stage application under 35 U.S.C. 371 and claims the benefit of PCT Application No. PCT/CA2020/051730 having an international filing date of Dec. 16, 2020, which designated the United States, which PCT application claimed the benefit of U.S. Provisional Application No. 62/951,560 filed Dec. 20, 2019, the disclosures of which are hereby incorporated by reference in their entireties.

FIELD

Apparatus and methodologies relating to thin film optical interference diagnostic devices are provided, and specifically to optical interference diagnostic devices incorporating porous anodic films and their methods of use.

BACKGROUND

The vast majority of biological samples from human patients, be it blood, urine, or tissue, continue to be tested and analyzed in large sophisticated laboratories, requiring highly trained staff and complex, expensive lab equipment. As such, there is a growing need for simple but reliable point-of-care (POC) diagnostic tools that can be used to test biological samples. It would be advantageous if such diagnostic tools could be used to test the biological samples as close as possible to the origin of the samples.

Many forms of POC diagnostic tools used in the detection of analytes in synthetic or biologic solutions are known, the bulk of which can be categorized into photometric, electrical-chemical based, and more recently developed microfluidic systems. To date however, such known POC diagnostic tools suffer from significant drawbacks. For example, although some POC diagnostic tools allow for diagnostic signals to be amplified for a more visible test result, such tools often require extensive sample preparation (e.g. for testing of whole blood samples) and can suffer from poor sensitivity.

Thin film optical interference devices, which are based upon the general phenomenon of light interference, have been proposed as a solution to the growing need for POC diagnostics tools. Known thin film devices operate by generating a 'colorimetric reading', or a change in the observable colour that is reflected off of the device due to, for example, the device being exposed to specific organic compounds or analytes. For example, having regard to FIG. 1 (PRIOR ART), an unreacted test surface (void of a detectable analyte) causes white light incident at the device to be reflected as gold (FIG. 1A). Alternatively, a reacted test surface exposed to a target analyte that binds to the surface of the device will cause the incident white light to be reflected as purple or blue (FIG. 1B). The observable colour change from gold to purple or blue is known as a 'colourimetric reading' and results due to the light interference difference between the unreacted and the reacted surfaces of the device. Herein, the term "colour change" relates to changes in colour hue and/or intensity ascertainable by the naked eye, or by other appropriate equipment that can be used to measure a change in the reflected wavelengths off of the surface of the device, e.g. a photometer, a spectrometer, or the like, as would be known in the art.

Colour changes produced by thin film devices vary depending upon changes in optical path length, which is dependent upon both the thickness of the film and/or the refractive index of the material being used. For example, optical interference can occur when a thin coating of translucent material is applied to an underlying opaque material having a different refractive index. Differences in the refractive index of two layers result in a reflection of light between the overlying semi-transparent material and the underlying opaque material. As the reflected light travels back out through the semi-transparent film it can interfere destructively or constructively with light reflected off of the front surface of the thin semi-transparent film. Visible colours can be generated this way via specific light wavelengths undergoing destructive or constructive interference. That is, the observed colour change occurs as a result of the light interference, which is dependent on the separation of the two reflecting surfaces, i.e. upon the thickness of the thin film, and upon the refractive indices of the materials being used.

As a result of the colourimetric readings generated, attempts have been made to use thin film optical interference devices as diagnostic tools in health-related applications. In such tools, the optically-active surface of the device is configured to exhibit a first colour and then, when exposed to a target analyte of interest, to generate a second colour caused by the analyte binding to the surface layer (i.e. a colorimetric reading).

Generally, early thin film diagnostic devices typically consisted of a thin layer of colour-generating material on a carrier wafer, and a layer of reagent material, such as a layer of antibody. At least one layer of additional dielectric material is then interposed between the colour-generating material and the reagent material, the thickness of each layer being sufficient enough that interference colours are observable. When the material to be detected, such as an antigen, is trapped as a thin layer by the reagent material, the interference effect is varied and a colour change is produced.

Unfortunately, early thin film diagnostic devices, such as those described in U.S. Pat. Nos. 3,979,184, 4,558,012, and 5,468,606, suffered from several problems, including a failure to account for refractive index differences between the target analyte being detected and the dielectric layer on the surface of the device. As such, to date, known thin film diagnostic devices are ineffective due to significant optical noise and reduced sensitivity.

Advancements to early thin film diagnostic devices have been made, including modifications allowing for improved control over the change in colour and for the change in colour to be maximized or "tuned". Although such modifications have helped to overcome some of the setbacks of the early thin film diagnostic devices by, inter alia, reducing optical noise and accounting for refractive indices of the devices, known devices nonetheless still require large, multi-layered devices that are costly and complicated to manufacture.

For example, having regard to FIG. 2 (PRIOR ART), which is partially reproduced from U.S. Pat. No. 5,124,172 (the "172 Patent"), a cross-sectional representation of commonly known thin film optical interference devices is shown. The device consists of at least three layers, the layers comprising a base layer made of glass or plastic, a middle layer of colour-generating metal, such as a layer of tantalum, and a top layer of anodizable metal, such as aluminum. Following anodization, the anodizable metal forms a porous anodized aluminum oxide-containing layer "AO", the anodic oxide AO serving to both increase the surface area to which a target analyte can bind, and also to produce both thickness and refractive index changes. The anodization also consumes some of the tantalum at the upper surface of the tantalum layer "T" to form a very thin barrier layer of tantalum oxide "TO".

Such early devices were valuable in demonstrating that where a change in thickness of the transparent anodic oxide AO is large enough, a noticeable change in the hue of the generated colour can be produced. These devices were also valuable in demonstrating that the sensitivity of the device can be increased when the type of anodic oxide AO is selected to provide a refractive index close to that of the target analyte, i.e. where the porosity of the oxide is adjusted to 'tune' the refractive index. That is, by tailoring the size and density of the porous film produced, the percentage of air in the film can be adjusted to tune the refractive index to be near that of the target analyte being detected. Tuning the refractive index generates more sensitive colour shifts, where even picomolar ($10^{-12}$) surface concentrations are observed.

Known devices require a layer of colour generating metal, such as tantalum T, niobium, titanium, zirconium, hafnium, vanadium, tungsten, molybdenum or alloys thereof, in order to generate an interference colour due to the absorption of light and relatively low reflectivity over the visible spectrum of light displayed by these metals. Such low reflectivity being utilized to balance the reflectivity of light off of the porous oxide surface and the light off of the underlying metal. However, these so-called colour generating metals tend to exhibit intense colours when covered by optically thin transparent layers due to both interference and absorption effects, which can dominate the colours produced by the porous anodic oxide and reagent layer on the surface.

Further, known devices are commonly manufactured using expensive and complicated physical vapour deposition techniques, such as atomic sputter deposition. Sputter deposition involves the bombardment of the target surface with energetic ions, resulting in the ejection of atoms, ions, or clusters of the target material from the surface. These atoms land on a substrate surface opposite the target material and a film starts to grow. The film will grow differently depending on the thermodynamic parameters of the deposit, the material properties of the substrate and target, as well as the processing parameters during sputtering (i.e. sputtering atmosphere, cathode and substrate geometry). As a result, the drawbacks and high costs of sputtering techniques to create complex, multi-layered thin film diagnostics limit the applicability and consumer market for such devices.

Thus, although the general concept of "tuning" changes to either the actual thickness and/or refractive index of the transparent anodic oxide AO to achieve a detectable colour change is known, early thin film devices nonetheless prove to be impractical for use as simple, rapid, and reliable POC diagnostic devices. There remains a need for the development of a simple, rapid, and reliable thin film optical interference device for use as POC diagnostic tools, and specifically for health-related applications. It is contemplated that advancements made in thin film optical interference devices generally may prove useful in the thin film POC diagnostic device space.

By way of example, the general concept of generating a colour change by altering the physical thickness of an optical interference film was also demonstrated in U.S. Pat. Nos. 4,066,816 and 4,310,586. These patents confirm that when manufactured to be of a sufficient thickness, oxide films on a layer of aluminum generate multi-colour interference effects, such effects arising between the light reflected off of the underlying aluminum layer and the light reflected off of the metal deposited thereon. These patents require a porous anodic oxide film of at least 3 microns, far too thick for the oxide to contribute to the interference colour, and therefore the colour generated is strictly due to the reflections off of the deposit and the underlying aluminum oxide/aluminum interface. Since the porous oxide is integral to the detection of the reagent layer, these patents are not suitable for use as diagnostic devices. Moreover, the interference effects are known to suffer from certain disadvantages, including a lack of colour uniformity and the procedure is difficult to control.

U.S. Pat. Nos. 5,167,793 and 5,218,472 (the "793 and '472 Patents", respectively) are directed to other known thin film optical interference devices developed for creating colour patterns on decorative articles or packaging, or for surface protection in architectural or automotive applications (i.e. decorative finishes, colour changes labels, transfer labels, moisture sensors, and temperature and time indicators).

For example, having regard to FIG. 3 (PRIOR ART), which is reproduced in part from the 793 Patent, known optical interference devices comprise an anodizable metal (e.g. aluminum) "B", which may or may not be coated onto the surface of a base layer, the anodizable metal anodized to form a porous anodic oxide "AO". A semi-reflective layer of a non-noble metal "NNM" is then deposited into the pores to generate a visible colour change. These devices are known to prove useful in creating a patterned or ornamental effect, where preselected areas of the film can be contacted with a noble metal to controllably replace the non-noble metal NNM (e.g. often referred to as a mask-less technique).

Although such techniques could potentially be used to generate enhanced interference colour ranges, higher colour saturation, and the production of patterned films that are less susceptible to colour loss (fading) or loss of colour uniformity, it remains unknown if such techniques could prove operative in the POC diagnostic device industry, i.e. whether such devices could be used for the detection of one or more target organic compounds.

As such, despite advancements made to thin film optical interference devices generally, to date, no known optical interference device provides a simple, rapid, and reliable thin film POC diagnostic apparatus and methodologies of use, such devices specifically operable to bind with, and thus detect, a target organic compound or analyte.

SUMMARY

According to embodiments, a thin film optical interference apparatus for use in detecting the presence of at least one compound is provided. In some embodiments, the apparatus comprises at least one layer of anodizable metal, the layer having at least a first portion that is anodized to form a porous metal oxide and at least a second portion that is non-anodized. The first portion of the layer may have a first thickness and a first refractive index generating at least one first optical path length, and the second portion of the layer may have a second thickness and a second refractive index generating at least one second optical path length. The at least one second optical path length may be different than the at least one first optical path length to cause a detectable colour change. When the apparatus is exposed to the at least one compound of interest, a third thickness and a third refractive index generates at least a third optical path length, the third optical path length being different than the first and second optical path lengths, and causing a colour change indicative of the at least one compound.

In some embodiments, the first portion of anodizable metal may be anodized to form at least one anodic pore. The at least one layer of anodizable metal may comprise a single layer of anodizable metal or metal-based alloy, such as aluminum, an aluminum-based alloy, or the like.

In some embodiments, the apparatus may further comprise at least one non-anodizable metal electrodeposited thereon. The electrodeposited metal may, for example, be selected from the group consisting of nickel, molybdenum, copper, and other metals.

According to embodiments, the use of a thin film optical interference apparatus to detect the presence of at least one compound is provided, the apparatus having a first thickness and a first refractive index. Use of the apparatus may comprise exposing a surface of the apparatus to at least one reagent material, the at least one reagent material causing the apparatus to have a second thickness and a second refractive index generating a second optical path length different from the first optical path length, and then contacting the surface of the apparatus with the at least one compound, said compound capable of binding to the at least one reagent material. Binding of the at least one compound and the reagent material may cause a third thickness and a third refractive index generating a third optical path length different from the first and second optical path lengths, the third optical path length causing a change in interference colour indicative of the presence of the at least one compound.

In some embodiments, the at least one compound may comprise an organic compound, wherein the one or more compounds are in a fluid. The fluid may comprise a biological fluid sample, such as a fluid sample selected from the group consisting of blood, urine, saliva, or tissue. In some embodiments, the apparatus may further be exposed to electrodeposition of a non-anodizable metal prior to the at least one reagent material.

According to embodiments, a method of manufacturing a thin film optical interference apparatus for detecting the presence of at least one compound is provided. The method may comprise providing at least one layer of anodizable metal, anodizing the at least one layer of anodizable metal to form a single-layer porous anodic film, and coating the resulting porous anodic film with a reagent material for binding with the at least one organic compound.

In some embodiments, the anodizable metal may be aluminum or an aluminum alloy, and anodizing of the anodizable metal may comprise anodically polarizing the metal in an electrolytic cell. The electrolytic cell may comprise an electrolyte selected from the group consisting of phosphoric acid, oxalic acid, sulfuric acid, or combinations thereof. In some embodiments, the method may further comprise the step of electrodepositing metal onto the apparatus, the electrodeposited metal being, for example, selected from the group consisting of nickel, molybdenum, copper, or other metals. In other embodiments, the method may further comprise performing the anodization step before, simultaneously with, or following the electrodeposition step.

BRIEF DESCRIPTION OF THE DRAWINGS

FIG. 1 (PRIOR ART) shows a diagrammatic representation of the light interference phenomenon (colourimetric reading) on the test surface of an optical interference apparatus, where an apparatus having an 'unreacted' test surface causes white light reflected at the device to be reflected as gold (FIG. 1A) and a 'reacted' test surface exposed to at least one target compound that binds to the surface causes white light reflected at the device to be reflected as purple or blue (FIG. 1B);

DETAILED DESCRIPTION OF THE PREFERRED EMBODIMENTS

Broadly, improved thin film optical interference apparatus and methodologies of use for detecting the presence of at least one compound are provided. Methodologies of manufacturing the present apparatus are also provided. The present apparatus and methodologies comprise means for generating optical interference colours directly on the surface of a single layer of anodized metal, eliminating the need for a layer of colour generating metal or any other colour-enhancing layering (e.g. eliminating the need for layers of tantalum, niobium, or the like). The interference colours generated by the present apparatus may be used to indicate the presence of at least one compound.

The present apparatus and methodologies may benefit from both the adjustment or tailoring of the refractive index of a porous anodic oxide film (through porosity) to be near that of the at least one compound being detected, and optionally, from strengthening of the interference colour generated using the deposition of at least one non-anodized metal into the pores of the anodic oxide film (i.e. to enhance the colorimetric reading generated by the devices). Advantageously, the apparatus and methodologies of use provide simple, effective, and reliable means for detecting small organic compounds, without the need of additional layers of colour generating materials, and without complex and expensive manufacturing processes (e.g. sputtering techniques).

The presently improved apparatus and methods of use will now be described in more detail having regard to FIGS. 4-6.

It is generally understood in the thin film optical interference device industry that strong interference colours are difficult to generate on devices having an aluminum base layer and an alumina surface layer because of the high reflectivity of the metal. The light reflected off of the aluminum surface overwhelms the light reflected off of the oxide surface, and therefore little to no interference colour can be observed. For this reason, aluminum is not considered to be a desirable surface for generating strong interference colours.

Counterintuitively, the present apparatus and methodologies of use aim to generate strong interference colours on an aluminum surface by, without limitation, a) using metallic alloys of lower reflectivity, b) depositing one or more non-anodized metal on top of or within the pores of the anodic oxide film to reduce the reflectance via scattering, c) using a polarizing filter to block out a significant portion of the light, i.e. block out p-polarized light such that s-polarized light reflected off of low index material is better observed, and/or d) viewing the apparatus at a low angle to improve reflectance off of low index material. It is an aim herein that the present apparatus and methodologies of use may provide a thin film optical interference apparatus operative as a POC diagnostic apparatus for detecting the presence of one or more compounds of interest.

Figure 2:
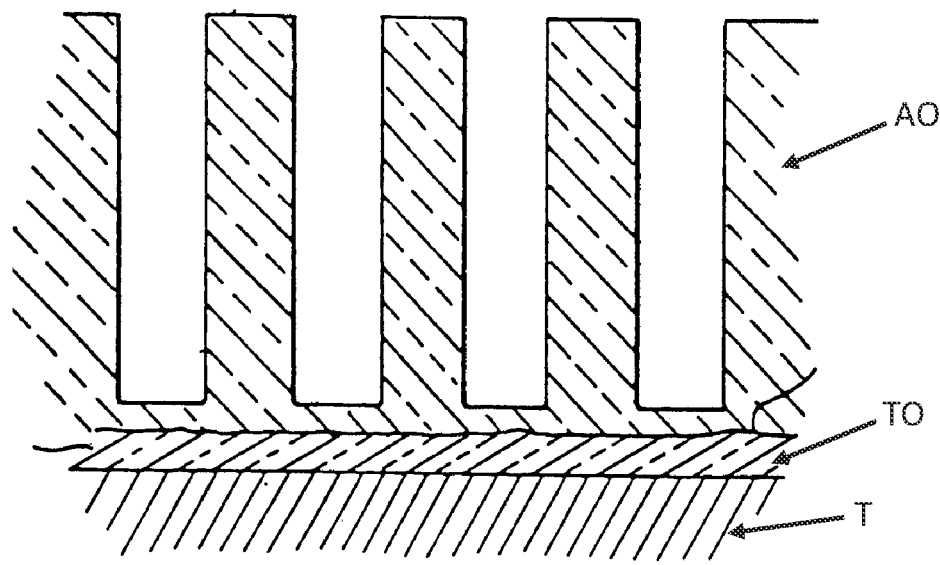
FIG. 2 (PRIOR ART) shows a diagrammatic cross-sectional representation of a known, multi-layered, porous-type anodic film device.
Figure 3:
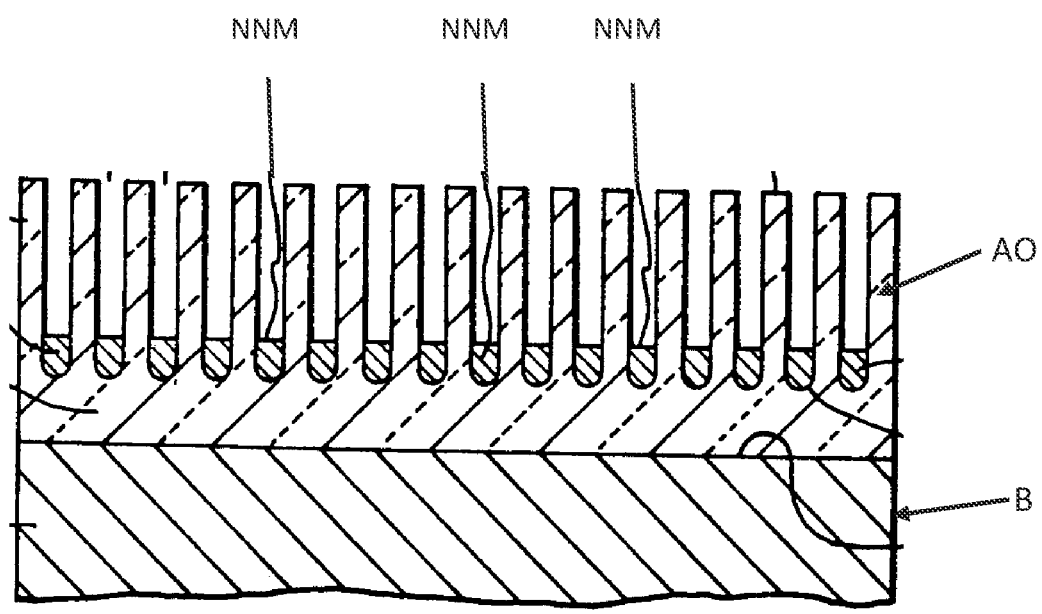
FIG. 3 (PRIOR ART) shows a diagrammatic representation of a porous-type anodic film device having non-noble metal deposits introduced into the porous anodic oxide layer.
Figure 4A:
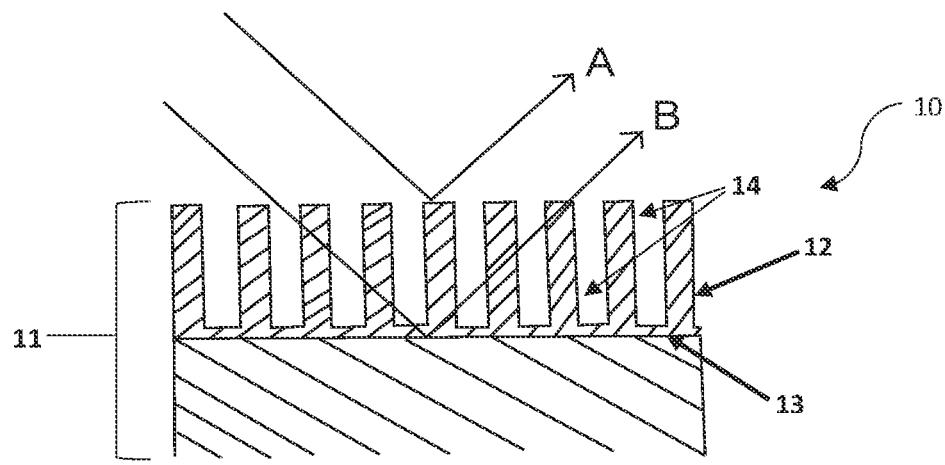
FIG. 4A shows a diagrammatic cross-sectional representation of the presently improved apparatus, the apparatus formed from a single layer of anodizable metal, a first portion of the metal being anodized to form a porous metal oxide, and a second portion of the metal that remains non-anodized and forms a metal substrate, according to embodiments.
Figure 4B:
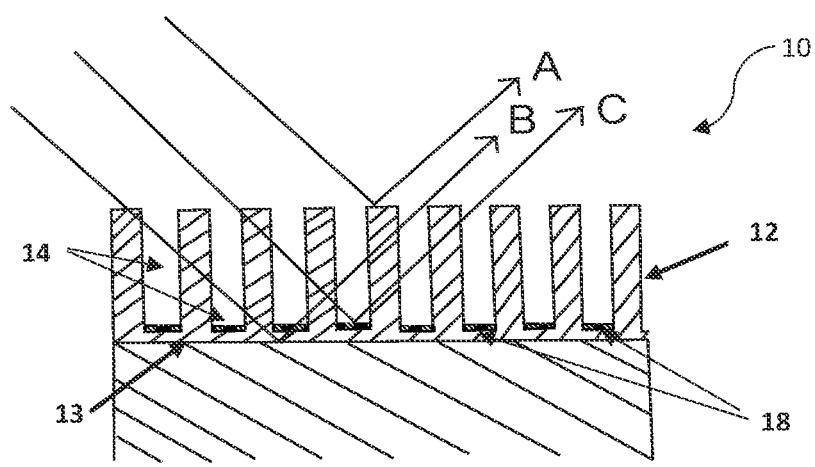
FIG. 4B shows a diagrammatic cross-section representation of the apparatus shown in FIG. 4A, the apparatus further having at least one metal deposited at or near the base of the anodic oxide pores formed in the anodized portion of the metal, according to embodiments.
Figure 4C:
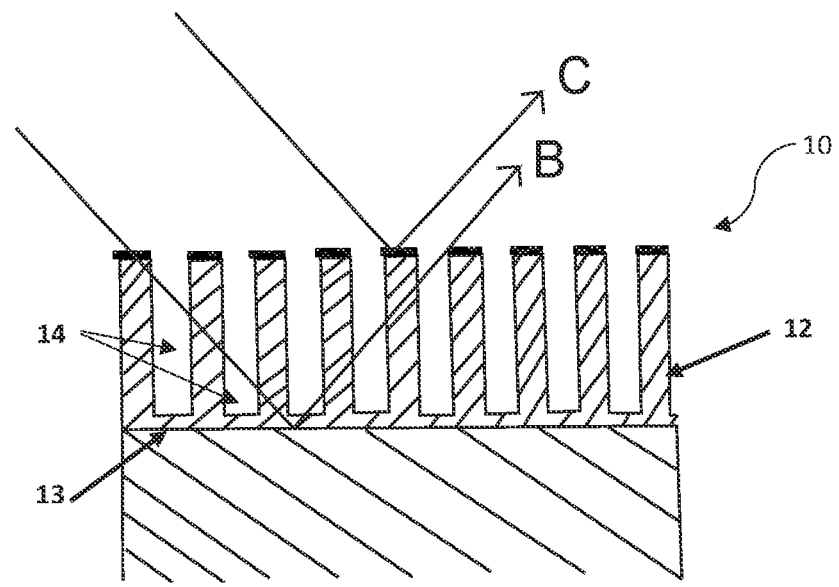
FIG. 4C shows a diagrammatic cross-section representation of the apparatus shown in FIG. 4A, the apparatus further having at least one metal deposited at or near the surface or mouth/opening of the anodic oxide pores formed in the anodized portion of the metal, according to embodiments.

Having regard to FIGS. 4A-C, the presently improved thin film optical interference apparatus 10 may comprise at least one layer of metal 11, and preferably a single layer of metal. The at least one layer of metal 11 may be anodizable, according to methods described herein. The at least one layer of metal 11 may, without limitation, be an anodizable layer of aluminum sheet metal, an aluminum-based alloy, or the like, such metal 11 initially having a smooth, uniform surface that can be anodized to form the apparatus and presently described.

The present apparatus 10 may comprise the at least one layer of anodizable metal 11 of aluminum or an aluminum-based alloy despite the understanding in the optical interference industry that strong interference colours are not consistently generated on the surface of such metals 13 due to their high reflectivity. It is contemplated that other suitable anodizable metals may be used, including metals where aluminum may not be the predominant metal.

The terms "metal" or "metal-based alloy" used herein are meant to relate to any materials that may be sufficiently reflective and planar for the intended use described, and any reference to "metal(s)" or "metal-based alloy(s)" is intended to collectively include any of the contemplated materials. Other examples of metals or metal alloys may comprise, without limitation, iron, stainless steel, nickel, cobalt, zinc, gold, copper, silver, titanium, etc, and alloys thereof. In some embodiments, the contemplated materials may comprise valve metals, or those metals that may be porous oxidized in a manner to tailor the refractive index. In some embodiments, the contemplated materials may comprise any optical substrate that is reflective only at its uppermost surface, and having a known refractive index.

Anodization: Having regard to FIG. 4A, the interference colours of the presently improved apparatus 10 may be generated directly on the surface of the at least one layer of anodizable metal 11. Anodization of the anodizable metal 11 can be done using known processes including the use of an electrolytic cell, where the metal to be oxidized is anodically polarized in an electrolyte. Anodization results in a first portion of the anodizable metal 11 forming an anodic film of aluminum oxide 12 and a second portion forming an aluminum metal surface 13, where competition between the growth of the anodic film and dissolution of the oxide by the acidic electrolyte creates the anodic oxide portion 12 having pores 14 that extend from the external surface of the film inwardly towards the interface with the metal surface 13 (i.e. the interface between the anodic oxide portion 12 and the non-anodized surface 13 of the metal 11). Light can then reflect off of the porous oxide surface of the anodized metal 12 (shown as line 'A'; FIG. 4A), as well as from the underlying metal surface 13 (shown as line 'B'; FIG. 4B), such reflections recombining to create interference colour effects.

Briefly, with regard to aluminum metal, it is generally understood that there are two main types of oxides that can be grown electrolytically using the anodization process: (i) barrier films, where a uniformly thick oxide layer grows on the aluminum surface, and (ii) porous films, where oxide growth occurs such that a regular array of pores develops. The type of oxide grown is determined by the nature of the electrolyte used, where neutral electrolytes, with a pH range of 5-7, grow barrier films and electrolytes in which aluminum oxide is sparingly soluble (phosphoric, sulphuric, oxalic, and chromic acids) will grow porous films. Typically, porous-type anodic aluminum oxide films form pores 14 that are essentially uniform in spacing, and having a barrier layer of aluminum oxide between the bottom of the pore 14 and the underlying surface of the metal 13.

The size and density of the pores 14 generated during the anodization process can depend on several factors including the electrolyte, pH, anodizing potential, time of anodization, and temperature used during the process. Pore 14 diameter tends to increase with an increase in electrolyte concentration, decrease in pH, increase in potential or increase in anodization time. The thickness of the aluminum oxide barrier 13 is linearly dependent on the anodization potential. As such, when considered and controlled, all of these factors can lead to tailorable nanostructured material, which can have strong effects on the optical properties of the resulting anodic film apparatus.

For example, when at least the foregoing factors are considered and controlled during the anodization process, pore size can be tailored such that compounds being detected are not entering the pores 14 and altering the effective refractive index of the alumina-air layer, but instead serve to increase the overall thickness of the film. Moreover, the size and density of the pores 14 can be adjusted such that the resulting refractive index of the alumina layer 12 matches that of the at least one compound being detected (as will be described).

Having further regard to FIG. 4A, as above, the single layer of anodizable metal 11 may form a first portion of non-anodized metal having a first thickness, resulting in a first optical path length (shown as line 'A'), and a second portion of anodized metal (i.e. forming porous metal oxide) having a second thickness and a second refractive index (and a second optical path length, shown as line 'B'). The second optical path length, being different than the first optical path length, may be controllably adjusted by the anodization parameters applied (e.g. time/duration and voltage of anodization). The controlled and tunable change in overall thickness and refractive index (i.e. the change in optical path length) results in a detectable colour change on the surface of the anodized metal, which might be observed as a yellow-orange colour. As will be demonstrated, when the apparatus 10 is then exposed to at least one target compound, and the compounds bind to the surface of the apparatus 10 to create a very small change in the thickness of the apparatus 10 (i.e. causing a third thickness and a third refractive index), a further detectable colour change may be generated, this time observed as dark purple, said colour change indicating the presence of the at least one compound.

Electrodeposition: According to some embodiments, optionally, the interference colours generated by the presently improved apparatus 10 may be enhanced to increase the colour saturation. Herein, the term 'colour saturation' relates to the colourfulness or perceived/detectable colour intensity generated by the presently improved apparatus 10 (i.e. the strength of destructive/constructive colour interference). In some embodiments, the colour saturation of the interference colours of the presently improved apparatus 10 may be enhanced using the electrolytic deposition of at least one metal into or near the pores of the anodized layer 12 during the manufacturing process. The electrodeposition process may occur simultaneously with or following the anodization process described above. In other words, anodization of the present apparatus 10 may be performed before, simultaneously with, or following the electrodeposition step.

Briefly, during manufacture of the present apparatus 10, the electrodeposition process may involve modifying the anodized metal 12 by depositing metal coatings 18 thereon using an electric current applied to a conductive material immersed in a solution containing a salt of the metal to be deposited. Electrodeposition can be used to create at least one semi-transparent film 18 within or on the pores of the anodized layer 12, such semi-transparent film 18 serving to distribute or scatter light traveling through the porous oxide layer 12 or reflected off metal surface 13. The semi-transparent film 18 may also serve to lower the reflectivity of the anodized metal 12, improving balancing of the light reflected off of the oxide and metal surfaces and creating a more strongly saturated colour. In some embodiments, electroless deposition may be used to create the at least one semi-transparent film 18 as described herein, although any other suitable means known in the art may also be used.

In some embodiments, electrodeposition may comprise immersing the anodized metal 12 in at least one appropriate solution, such as an acidic solution with a metal salt. In some embodiments, the solution may comprise a metal salt including, without limitation, a salt of nickel, molybdenum, tin, cobalt, etc., or combinations thereof. In some embodiments, electrodeposition may comprise providing or applying an alternating current with a counter electrode, such electrode being any known electrode suitable in the art including, without limitation, graphite or metal. It should be understood that the electrode should comprise a metal of the same type as the metal salt in the electrolyte.

Figure 4D:
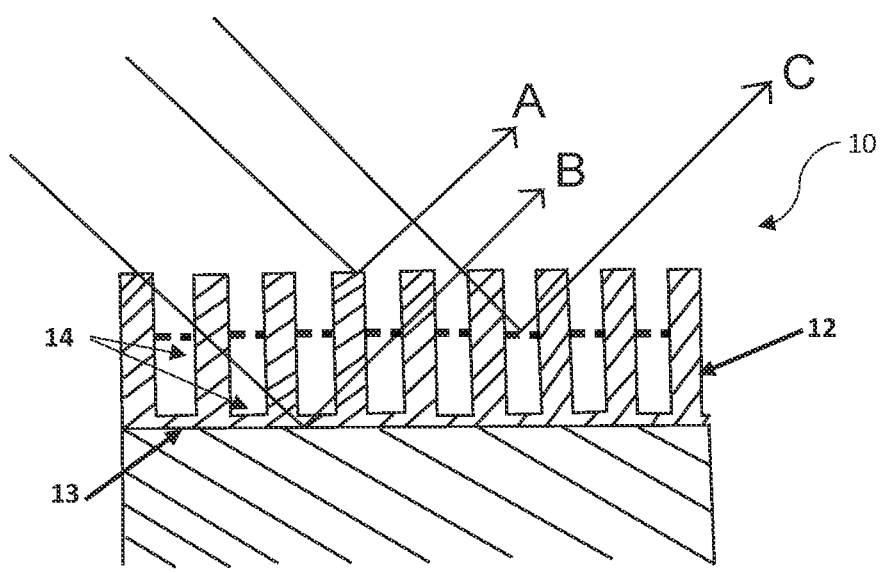
FIG. 4D shows a diagrammatic cross-section representation of the apparatus shown in FIG. 4A, the apparatus further having at least one metal deposited at one or more areas within the anodic oxide pores formed in the anodized portion of the metal, according to embodiments.

As above, the presently improved apparatus 10 may be configured such that light can reflect off the porous oxide surface of the anodized metal 12 (shown as line 'A') and off of the metal surface 13 (shown as line 'B'), which contributes to the interference colour (i.e. wherein the at least one second optical path length CB' is different from the at least one first optical path length CA' to cause a detectable colour change). Having specific regard to FIGS. 4B, 4C and 4D, such interference colours may then be enhanced when the present apparatus 10 is electrodeposited with a metal 18, the metal being deposited, without limitation, at or near the base of the pores 14 formed in the anodized metal 12 (FIG. 4B), at or near the top or opening of the pores 14 (FIG. 4C), or at any other location within the pores 14 as may be desired (FIG. 4D).

For example, in some embodiments, having regard to FIG. 4B, the presently improved apparatus 10 may be configured such that light can reflect off the porous oxide surface of the anodized metal 12 (shown as line 'A'), off of the metal surface 13 (shown as line 'B'), and further off of the deposited metal 18 (shown as line 'C'), the deposited metal 18 serving to enhance the interference colour or detectable colour change generated). In other embodiments, having regard to FIG. 4C, the presently improved apparatus 10 may be configured such that light can reflect off the surface off of the porous oxide surface of the anodized metal 12 (shown as line 'B'), and off of the surface of the deposited metal 18 (shown as line 'C'). In yet other embodiments, having regard to FIG. 4D, the presently improved apparatus 10 may be configured such that light can reflect off of the surface of the porous oxide surface of the anodized metal 12 (shown as line 'A'), off of the surface of the metal 13 (shown as line 'B'), and further off of the deposited metal 18 (shown as line 'C'). According to embodiments, the electrodeposition of the deposited metal 18 aims to enhance the interference colour generated by light reflecting off the porous oxide surface of the anodized metal 12 (shown as line 'A') and off of the metal surface 13 (shown as line 'B'), creating a more strongly saturated colour.

In some embodiments, the presently anodized metal 12 may be electrodeposited with any suitable metal 18 including, without limitation, nickel, molybdenum, copper, and other metals as may be appropriate in the art for electrodeposition. Preferably, the presently anodized metal 12 may comprise aluminum and the non-anodizable metal to be electrodeposited may comprise nickel.

Analyte Detection: As will be described, having regard to FIGS. 5 and 6, an increase in both film thickness and refractive index, resulting in a further change in interference colours (i.e. an observable colour change), can result from the binding of a reagent material and a layer of at least one compound to be detected to the porous surface layer of apparatus 10. That is, when a very thin layer of at least one compound is absorbed in at least one location on the porous surface layer (i.e. at the air oxide interface and/or inside the pores 14) the apparatus 10, a change in the first optical path length CA' can be produced, and a colour change can be observed. Accordingly, as will be described in more detail, the present apparatus 10 may be used for detecting the presence of at least one target organic material, compound, and/or analyte, such presence being indicated by the generation of a detectable colour change.

Figure 5A:
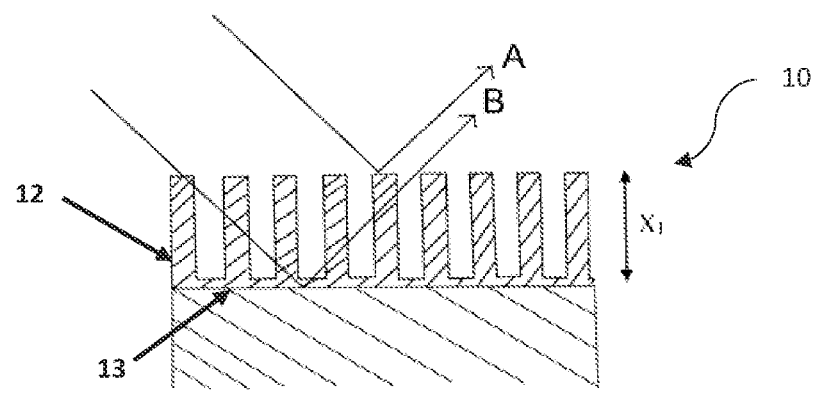
FIG. 5A shows a diagrammatic cross-section representation of the apparatus as shown in FIG. 4A, the apparatus having a first structural thickness ($X_1$), according to embodiments.
Figure 5B:
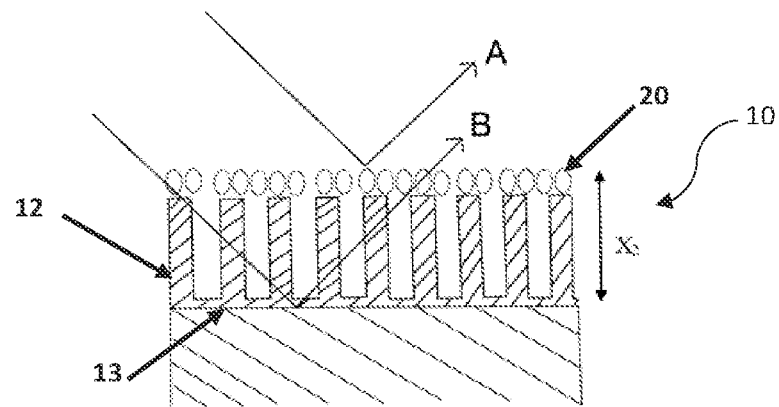
FIG. 5B shows a diagrammatic cross-section representation of the apparatus shown in FIG. 5A, the apparatus further comprising a reagent material of interest (e.g. an antigen) and having a second structural thickness ($X_2$), according to embodiments.
Figure 5C:
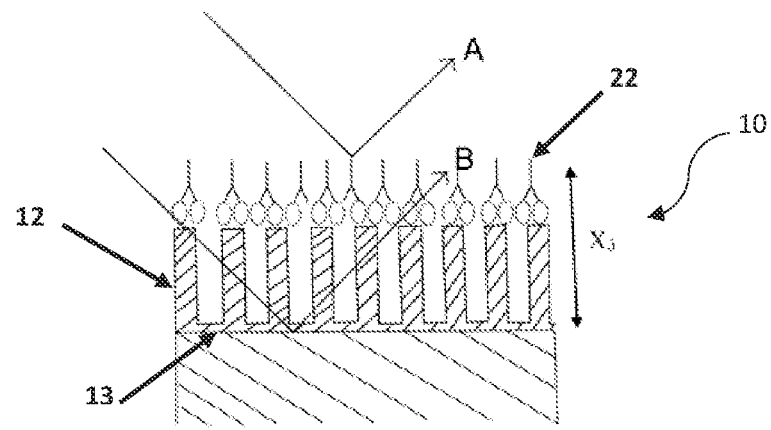
FIG. 5C shows a diagrammatic cross-section representation of the apparatus shown in FIG. 5B, the apparatus having been exposed to at least one compound of interest (e.g. an antibody bound to the antigen), and having a third structural thickness ($X_3$), according to embodiments.

Having regard to FIGS. 5A, 5B, and 5C, the presently improved apparatus 10 may be used as a simple, effective point-of-care (POC) optical immunoassay to detect the presence of a broad range of compounds of interest. For example, having regard to FIG. 5A, at least one presently improved apparatus 10 of anodizable metal 11 is produced using the anodization process described herein. As above, an initial interference colour is generated via the interference between reflections, i.e. light reflected off of the first portion of the anodizable metal 11 that is anodized to form a porous oxide surface of the anodized metal 12 (shown as line 'A') and off of the second portion of the anodizable metal 11 that is non-anodized to form a metal surface 13 (shown as line 'B'). Following anodization, the apparatus comprises a first thickness ($X_1$), and generates a first detectable colour change.

Having regard to FIG. 5B, where it is desired to detect at least one compound, the surface of the present apparatus 10 may be exposed to at least one reagent material (e.g. an antigen) 20, for binding with said at least one compound. The apparatus 10 exposed to the reagent material 20 may have a slightly larger thickness ($X_2$), relative to the apparatus 10 without the reagent material 20. The apparatus 10 exposed to the reagent material 20 may also have a change in the optical path length, relative to the apparatus 10 without the reagent material 20 (shown as line 'B'). The change in thickness and optical path length can result in a different interference colour, generating a second detectable colour change (such colour change thus providing an effective baseline colour for use in detecting the presence of at least one compound).

Having regard to FIG. 5C, once the apparatus 10 has been exposed to at least one reagent material 20, the apparatus 10 may then be exposed to or contacted with at least one target compound 22 (e.g. an antibody) capable of binding to or with the reagent material 20 (e.g. antigen). The apparatus 10 exposed to the at least one target compound 22 may again have a larger, third thickness ($X_3$), relative to the apparatus 10 without the at least one compound 22. The apparatus 10 exposed to the at least one compound 22 may also have a change (e.g. an increase) in the optical path length (shown as line 'B'), relative to the apparatus 10 without the at least one compound 22. Again, the even further change in thickness $X_3$ and optical path length (line 'B') can result in yet another different interference colour (as compared to the apparatus 10 having thickness $X_2$ or $X_1$). That is, the change in thickness and optical path lengths resulting from the binding of the at least one compound 22 can result in a different interference colour being generated, causing a detectable colour change from the effective baseline detectable colour (when only the reagent material 20 is present), such detectable colour change from baseline thus being indicative of the presence of the at least one compound 22.

Figure 6A:
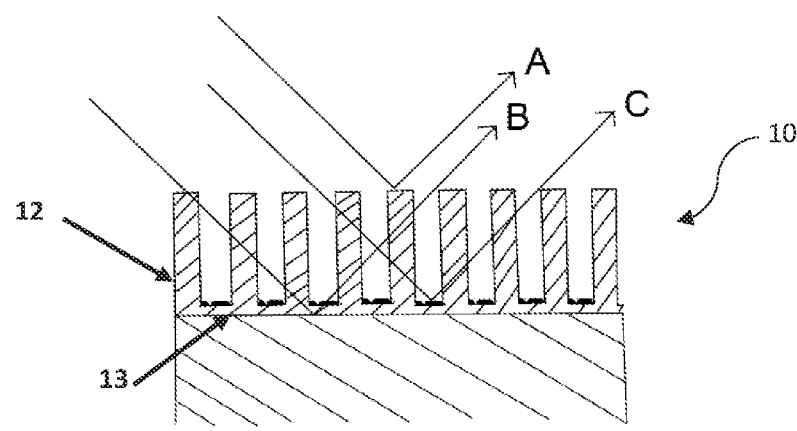
FIG. 6A shows a diagrammatic cross-section representation of the apparatus as shown in FIG. 4B, the apparatus having a first structural thickness ($X_1$), according to embodiments.
Figure 6B:
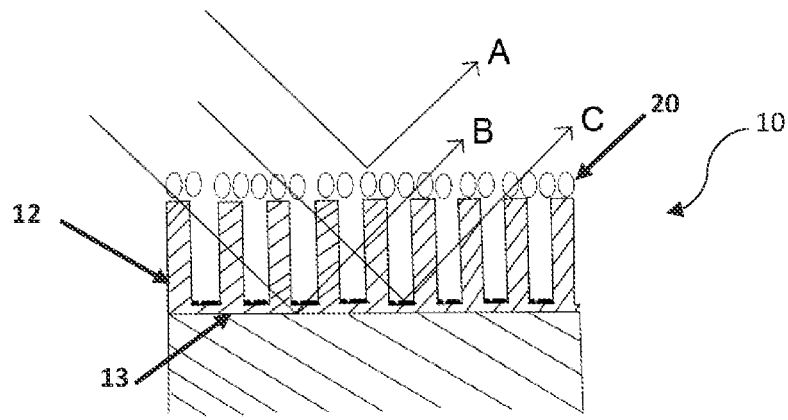
FIG. 6B shows a diagrammatic cross-section representation of the apparatus shown in FIG. 6A, the apparatus further comprising a reagent material of interest (e.g. an antigen) and having a second structural thickness ($X_2$), according to embodiments.
Figure 6C:
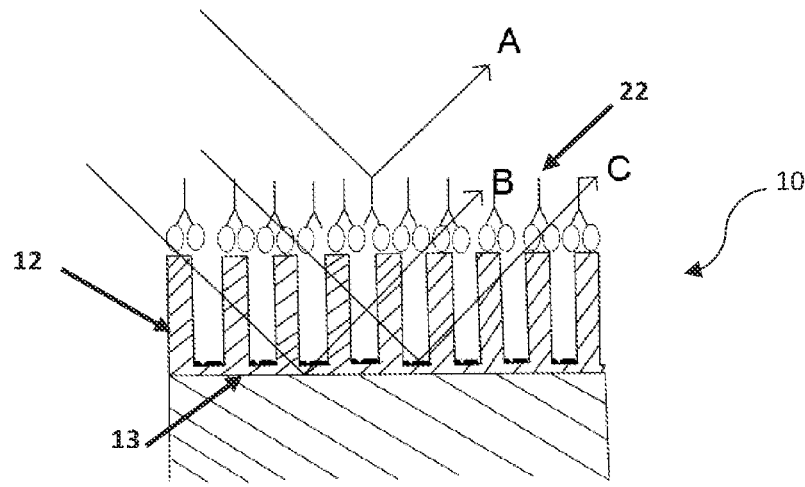
FIG. 6C shows a diagrammatic cross-section representation of the apparatus shown in FIG. 6B, the apparatus having been exposed to at least one compound of interest (e.g. an antibody bound to the antigen), and having a third structural thickness ($X_3$), according to embodiments.

In further embodiments, having regard to FIGS. 6A, 6B, and 6C, the use of the presently improved apparatus 10 as a simple, effective point-of-care (POC) optical immunoassay to detect the presence of a broad range of compounds of interest may be enhanced by electrodepositing a non-anodized metal 18 onto the apparatus 10. For example, having regard to FIG. 6A, at least one presently improved apparatus 10 of anodizable metal 12 is produced using the anodization process described herein. As above, an initial interference colour is generated via the interference between reflections, i.e. light reflected off of the porous oxide surface of the anodized metal 12 (shown as line 'A') and off of the metal surface 13 (shown as line 'B'). In some embodiments, as above, the present apparatus 10 may be configured such that light also reflects off of the deposited metal 18 (shown as line 'C').

Having regard to FIG. 6B, where it is desired to detect at least one compound 22, the surface of the present apparatus 10 may be exposed to at least one reagent material (e.g. an antigen) 20, for binding with said at least one compound 22. The apparatus 10 exposed to the reagent material 20 may have a slightly larger thickness ($X_2$), relative to the apparatus 10 without the reagent material 20. The apparatus 10 exposed to the reagent material 20 may also have a change in the optical path length, relative to the apparatus 10 without the reagent material 20 (shown as line 'B'). The change in thickness and optical path length can result in a different interference colour.

Having regard to FIG. 6C, once the apparatus 10 has been exposed to at least one reagent material 20, the apparatus 10 may then be exposed to or contacted with at least one target compound 22 (e.g. an antibody) capable of binding to or with the reagent material 20 (e.g. antigen). The apparatus 10 exposed to the at least one target compound 22 may again have a larger thickness ($X_3$), relative to the apparatus 10 without the at least one compound 22. The apparatus 10 exposed to the at least one compound 22 may also have a change (e.g. an increase) in the optical path length (shown as line 'B'), relative to the apparatus 10 without the at least one compound 22. Again, the even further change in thickness $X_3$ and optical path length (line 'B') can result in yet another different interference colour (as compared to the apparatus 10 having thickness $X_2$ or $X_1$), such different interference colour being enhanced relative to the apparatus 10 without the electrodeposited non-anodized metal 18 (e.g. relative to the apparatus 10 shown in FIG. 5C).

Without limitation, it is contemplated that the presently improved apparatus 10 may be used to detect the presence of a broad range compounds 22, such as specific binding pair assays (e.g. antigen or antibody detection), for the detection of enzymatic activity, or for the detection of small organic molecules (e.g. drugs of abuse, therapeutic drugs, or environmental agents), or the like.

In some embodiments, the at least one compound detected may or may not be in a sample, such as a fluid sample. In some embodiments, the fluid sample may comprise a biological sample, and may be any biological fluid sample including, without limitation, a biological fluid sample of blood, urine, saliva, or tissue.

According to embodiments, the presently improved apparatus 10 may be used to detect the presence of at least one compound, the use comprising exposing a surface of the apparatus 10 to at least one reagent material 20, and then contacting the surface of the apparatus 10 with the biological fluid sample containing the at least one target compound 22. In some embodiments, the at least one reagent material 20 may comprise any appropriate reagent material 20 known in the art that can interact with, i.e. can bind to, the at least one target compound 22 to generate an increase in thickness and in refractive index of the apparatus 10, resulting in a detectable colour change.

According to embodiments, the presently improved apparatus 10 may be used to detect the presence of at least one compound 22, including the detection of compounds that form complexes on the surface of the apparatus 10. In some embodiments, complexes formed on the surface of the apparatus 10 may comprise, for example, antigen-antibody, aptamer-antigen, protein-protein, toxin-receptor, enzyme-receptor and enzyme-substrate. In other embodiments, use of the presently improved apparatus 10 to detect at least one compound 22 may be designed and/or specifically tailored as a tool to both detect and diagnose various health-related conditions such as antibody mediated rejection of solid transplant organs via the detection of donor-specific HLA (human leukocyte antigen) antibodies, the exposure to various diseases such as Zika virus, or other infectious diseases, through an antibody (IgG or IgM) mediated response, and the detection of biomarkers for malignant cancers (i.e. PDGFR-alpha), which is highly correlated to metastasis in papillary thyroid cancer.

In order to ensure binding of the at least one compound 22 to the surface layer of the apparatus 10, physical adsorption or immobilization of the at least one compound 22 using standard binding techniques can be used. For example, the surface of the apparatus 10 may be exposed to the at least one reagent material 20 in a suitable solvent and left for a period of time (i.e. up to 24 hours). Following the desired exposure time, the surface of the apparatus 10 can be rinsed with a rinsing agent (e.g. deionized water or buffer) to remove any excess reagent material 22 therefrom. In some cases, the rinsing agent may also contain a detergent such as Tween 20 to help remove any unbound reagent material 20. Reagent materials 20 that may be found to bind strongly to the surface of the apparatus 10 can include vitamin K dependent agents 20, however, strong binding is not limited to these materials 20.

For detection of the at least one compound 22 on the surface of the apparatus 10, the sample of compound 22 may be exposed to the surface at or near the area where the reagent material 22 has bound for a suitable period of time (e.g. from a few seconds up to 24 hours, or other such periods of time depending on the application). The sample of at least one compound 22 may then be removed from the surface of the apparatus 10 by rinsing the apparatus 10 with a rinsing agent (e.g. deionized water or buffer) and the apparatus 10 is allowed to dry.

It should be appreciated that any materials used in the presently improved optical interference apparatus are chemically inert and do not affect any biochemical reaction resulting from the use of the present apparatuses.

The present apparatus and methodologies will now be illustrated in more detail by way of the following Examples. Example parameters, such as measurement, voltages, temperature, and pressure ranges, are provided for explanatory purposes only and are not intended to limit the scope of the subject technology in any way.

EXAMPLES

Example 1

This Example illustrates the sensitivity of the present apparatus to small changes in thickness (e.g. 1-100 nm) resulting in colour changes of the surface.

By way of background, the anodization process can be carried out in an electrolyte containing a suitable acid including, without limitation, phosphoric, oxalic, sulfuric, or combinations thereof. In some embodiments, phosphoric acid may be desirable due to its ability to produce alumina films that are highly porous, resistant to hydrating, and relatively inert in aqueous environments. Higher porosities may allow for lower refractive indices, as more air is incorporated into an alumina-air layer. Moreover, the oxide produced is inert in aqueous environments due to the resulting phosphate incorporated into the film from the electrolyte, whereby the stability of the films in aqueous environments can be increased by incorporating more phosphate ions in the alumina. As a skilled person in the art would know and appreciate, although certain electrolytes are described herein, any suitable electrolyte containing an appropriate acid is contemplated.

In some embodiments, anodization may be carried out at any suitable voltage, and preferably at a constant voltage of up to 150V. Anodization may be performed until a porous oxide layer is created on the surface of the anodizable metal 11. As will be demonstrated, light can then be reflected off of the oxide surface (line 'A'), as well as from the underlying substrate (line 'B'), and these reflections recombine and create interference colour effects.

Herein, a 1.5 cm by 6 cm coupon of aluminum 28 gauge, AA3003 sheet metal having a smooth, uniform surface was anodized in 1M phosphoric acid ($H_3PO_4$) at a constant voltage of 4V DC and a temperature of 18° C. for an anodization time of 7 minutes to produce a porous anodic film of 120 nm in thickness. A 'sufficient thickness' of aluminum sheet metal may comprise approximately 300 nm in size or, as would be appreciated, any sufficient thickness to ensure an optically thick metal layer remains following anodization, i.e. a layer operative to generate a reflection at the oxide/metal surface.

The aluminum sheet metal was rinsed thoroughly with deionized water and allowed to air dry. Following anodization, the sheet was observed at an angle of approximately 75° (i.e. with a near-perpendicular angle from the surface normal) under white light and found to be yellow-orange in colour. The refractive index and porosity of the anodic film was measured using ellipsometry and found to be 1.26 ($\lambda$=555 nm) and 60% respectively. The effective refractive index of the alumina-air composite film can be represented by the following equation:

$$\eta_{eff} = \eta_{air} x + \eta_{alumina}(1-x)$$

Where $\eta_{eff}$ is the effective refractive index of the porous alumina layer, $\eta_{air}$ is the refractive index of air (1.0003, $\lambda$=589 nm), $\eta_{alumina}$ is the refractive index of the aluminum oxide, and x is the porosity of the film. In this manner, the refractive index of the aluminum oxide is calculated to be 1.65. As seen in the equation, the porosity of the film changes the effective refractive index from 1.65, if it was pure aluminum oxide (x=0), to 1.26, thereby demonstrating the ability of these films to have tailorable refractive indices.

The anodized aluminum metal was then exposed to various solutions containing compounds or analytes of different sizes (units of mass) including deoxycholic acid (2.5% w/v, MW=392.6 Da), phosvitin (200 µg/mL, MW=35 000 Da), or human prothrombin (200 µg/mL MW=72 000 Da) for 15 minutes. Following exposure, the anodized metals were rinsed with deionized water and allowed to dry. The sheet was again observed at an angle of approximately 75° from normal under white light where the sheets exposed to deoxycholic acid were observed to be dark purple in colour, the sheets exposed to phosvitin were observed to be red in colour, and the sheets exposed to prothrombin were observed to be purple in colour.

Example 1 demonstrates that the presently anodized aluminum sheet metals are sensitive to very small changes in thickness and refractive indices from adsorbed biomolecules. Example 1 further demonstrates how the presently anodized aluminum sheet metals can generate colour changes as a result of small variations in compound size (e.g. molecular weight).

Example 2

Example 2: This Example illustrates how the present apparatus can be used for the detection of an immune complex forming on the surface between antigen and antibody.

A plurality of anodized aluminum sheet metal apparatuses were made as outlined above in Example 1.

Each anodized aluminum sheet metal was exposed to a solution containing human prothrombin (200 µg/mL in Tris buffered saline (TBS)) for 15 minutes. Following the exposure, the aluminum sheet metal was rinsed with deionized water and allowed to dry. The sheet metal was again observed at an angle of approximately 75° from normal and, in each case, a purple colour was observed.

Each anodized aluminum sheet metal was then exposed to an organic compound or analyte of interest, namely, either anti-human prothrombin IgG or a non-immune IgG (e.g. Rabbit Anti-Sheep IgG Fc) at 200 µg/mL in TBS for 15 minutes. The sheet metal was again observed at an angle of approximately 75° from normal. Those devices that were exposed to anti-human prothrombin were observed to be a blue colour, while those devices exposed to a non-immune IgG did not create a colour change.

Example 2 demonstrates that the present apparatus are sensitive to the detection of the presence of an immune complex.

Example 3

Example 3: This Example illustrates improved colour interference created by the present apparatus when a metal is electrodeposited into the pores of the present porous anodic films.

As above, in the electrodeposition process, non-anodizable metal may be deposited into and/or around the pores of the anodic oxide film by the passage of electric current. Without being limited to theory, it is understood that the colour interference of such electrodeposited films occurs between light scattered from the individual deposit surfaces (line 'C') and light scattered from the anodized metal 12 (line 'A') and the metal surface 13 (line 'B'). As such, the colour produced may depend upon the difference in optical path resulting from separation of the two light scattering surfaces as a complement to the colour, thereby enhancing the interference colours being generated.

Prior to testing, a plurality of aluminum metal 38 gauge (0.102 mm thick) foil samples (1.5 cm by 6 cm) were adhered to a polystyrene backing using an acrylic adhesive. The aluminum foil samples were anodized in 1M phosphoric acid ($H_3PO_4$) at a constant voltage of 4V DC at temperature of 17° C. In order to generate devices having varied background colours, several devices were anodized for 6 minutes, other devices were anodized for 7 minutes, and still others were anodized for 8 minutes.

As shown in Table 1, each of the devices anodized for 6 minutes had an original surface colour of faint yellow, while devices anodized for 7 and 8 minutes, respectively, had an original surface colour of faint golden yellow. As will be shown below, it should be appreciated that the longer anodization times of 7 and 8 minutes resulted in thicker anodized alumina and a larger optical path length, which generate different interference colours following the electrodeposition process due to the differences in optical path length. However, as may be observed in Table 1, the colour variation with increased anodization time is initially minimal without electrodeposition i.e. yellow (6 minutes), golden yellow (7 minutes) and golden yellow (8 minutes).

Following anodization, half of the anodized aluminum apparatuses were subjected to the electrodeposition of nickel using a nickel salt solution (25 g/L nickel sulphate hexahydrate, 20 g/L magnesium sulphate heptahydrate, 25 g/L boric acid, 15 g/L ammonium sulphate, 1 g/L tartaric acid) at a voltage of 9V AC peak, 60 Hz, for a duration of 1 minute (60 seconds).

As shown in Table 1, electrodeposition of the apparatuses resulted in a colour change from faint yellow to a brighter golden yellow (devices anodized for 6 minutes), from faint golden yellow to red (devices anodized for 7 minutes), and from faint golden yellow to purple (devices anodized for 8 minutes).

Each of the anodized aluminum apparatuses were then exposed to a solution containing human prothrombin (200 µg/mL) for a period of 15 minutes. The apparatuses were then rinsed with deionized water and dried.

As shown in Table 1, coating the surface of the anodized devices with prothrombin resulted in detectable colour changes. Exposing anodized devices without electrodeposition to prothrombin resulted in a colour change from faint yellow to faint beige (devices anodized for 6 minutes), from faint golden yellow to faint purple (device anodized for 7 minutes), and from faint golden yellow to purple (devices anodized for 8 minutes). Exposing anodized devices with electrodeposited nickel to prothrombin resulted in a colour change from golden yellow to red (devices anodized for 6 minutes), from red to purple (devices anodized for 7 minutes), and from purple to blue (devices anodized for 8 minutes).

Each of the anodized aluminum devices were then exposed to an organic compound or analyte of interest, namely, anti-human prothrombin IgG (200 mcg/mL), via a drop of the compound being placed on the prothrombin coated surface of the devices for a period of 15 minutes. Following exposure to the compound, the devices were washed with deionized water and allowed to air dry.

As shown in Table 1, exposing anodized devices without electrodeposition to anti-human prothrombin IgG resulted in a colour change from faint beige to faint pink (devices anodized for 6 minutes), from faint purple to faint dark purple (device anodized for 7 minutes), and from purple to faint blue (devices anodized for 8 minutes). Such colour changes again confirming the detection of an immune complex forming between antigen and antibody on the surface of the present devices (see Example 2).

Exposing anodized devices with electrodeposited nickel to anti-human prothrombin IgG resulted in clear, enhanced colour changes from red to purple (devices anodized for 6 minutes), from purple to blue (devices anodized for 7 minutes), and from blue to cyan (devices anodized for 8 minutes).

TABLE 1

| Anodization Time (min) | Original Surface Colour | Colour After Human Prothrombin | Colour After Anti-Human Prothrombin IgG |
|---|---|---|---|
| 6 min | Faint yellow | Faint beige | Faint pink |
| 6 min + 60 s Nickel Deposition | Golden yellow | Red | Purple |
| 7 min | Faint golden yellow | Faint purple | Faint dark purple |
| 7 min + 60 s Nickel Deposition | Red | Purple | Blue |

TABLE 1-continued

| Anodization Time (min) | Original Surface Colour | Colour After Human Prothrombin | Colour After Anti-Human Prothrombin IgG |
|---|---|---|---|
| 8 min | Faint golden yellow | Purple | Faint blue |
| 8 min + 60 s Nickel Deposition | Purple | Blue | Cyan |

The foregoing Examples demonstrate that interference colour changes resulting from the formation of the immune complexes on the surface of the present apparatuses are more difficult to observe at areas of anodized aluminum without nickel deposition, compared to those areas having nickel deposition. Herein, the present Examples show improved colourimetric reading (colour saturation and visible interference) achieved by the present devices and methods of use in detecting the binding of immune complexes.

It should be understood that a combination of yellow/gold interference colours for the test surface background or starting point are known, and are particularly useful as a change from such a background colour (e.g. to a purple/blue colour) can typically be observed by the naked eye. It is contemplated, however, that the present devices can be adjusted and optimized in any manner known in the art in order to optimize the background starting colour, the observable colour change, or both.

Example 4

Example 4: This example illustrates how the colour interference in the present apparatus 10 may be further modified during the manufacturing process by continued anodization after the deposition of a metal 18 into the pores 14 of the present apparatus 10.

Prior to testing, a plurality of aluminum metal 38 gauge (0.102 mm thick) foils were laminated to a polymer backing on one side. The aluminum foil samples were then anodized in a 1M phosphoric acid ($H_3PO_4$) solution at a constant voltage of 4V DC at a temperature of 14° C. for 8 minutes each. The anodized aluminum devices were then subjected to electrodeposition of nickel using a nickel salt solution following the same procedure as Example 3. When viewed from a 75° angle to normal, the colours of the devices were faint yellow without nickel deposition and vivid golden yellow with the nickel deposition.

After deposition, the deposited nickel was replaced with palladium by an immersion plating process. An acidic solution of $PdCl_2$ was prepared, comprised of 500 ppm $PdCl_2$ and 0.1 M HCl in deionized water. The devices were dipped in the solution for 45 seconds. Afterwards, the devices appeared a slightly more vivid golden yellow colour when viewed from a 75° angle to normal. The devices were then further anodized in a 1M phosphoric acid ($H_3PO_4$) solution at a constant voltage of 12V DC at a temperature of 14° C.; some devices were anodized for 4 minutes and some for 6 minutes. The devices anodized for 4 minutes appeared as a pale blue when viewed from the surface normal and a pale pink when viewed from a 75° angle to normal. The devices anodized for 6 minutes appeared as a faint green-yellow when viewed from the surface normal and a deep purple when viewed from a 75° angle to normal.

Each of the anodized apparatuses were exposed to a 200 µg/mL solution of prothrombin in TBS buffer for 15 minutes. The apparatuses were then rinsed with distilled water and dried.

The surface of the apparatuses could be seen to change after exposure to prothrombin. The apparatuses anodized for 4 minutes after the metal deposition appeared as a magenta, while the apparatuses anodized for 6 minutes after the metal deposition appeared as a cyan.

This example demonstrates that the present apparatuses can be adjusted to optimize the background starting colour, the observable colour change, or both.

Advantageously, it is contemplated that the presently improved apparatus 10 may be created having diffuse reflecting surface as opposed to a specular reflecting surface, as interference colours can then be viewed at any angle from the surface of the apparatus 10 due to a general scattering of the light. As would be appreciated, methods of creating a diffuse surface may include physical abrasion, chemical abrasion, or coating of a material on the surface. It is contemplated that a multitude of industries may benefit from the present simple, affordable, and accessible apparatus 10 and its methodologies of use. Such industries might include, without limitation, environmental, health, and scientific research industries.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and the described portions thereof.

What is claimed is:

1. A thin film optical interference apparatus for detecting the presence of a target compound, the apparatus comprising:
   a single layer of an anodizable metal, the layer having a first portion that is anodized to form a porous metal oxide and a second portion that is non-anodized underlying the first portion; wherein
   the first portion of the layer comprises a first thickness and a first refractive index generating a first optical path length,
   the second portion of the layer comprises a second thickness and a second refractive index generating a second optical path length;
   wherein the second optical path length is different than the first optical path length providing a first interference colour, and
   a non-anodized metal electrodeposited on the porous metal oxide providing an enhanced interference colour compared to the first interference colour; and
   wherein upon binding of the target compound to the apparatus, a third thickness and a third refractive index generates a third optical path length, the third optical path length being different than the first and second optical path lengths, resulting in a detectable change in interference colour indicative of the presence of the target compound.

2. The apparatus of claim 1, wherein the single layer of the anodizable metal comprises aluminum or an aluminum-based alloy.

3. The apparatus of claim 2, further comprising a reagent material on the porous metal oxide, the reagent material being capable of binding to the target compound, and providing a second interference colour different from the first interference colour, wherein the electrodeposited metal provides an enhanced interference colour compared to the second interference colour.

4. The apparatus of claim 3, wherein the electrodeposited metal is selected from the group consisting of nickel, molybdenum, and copper.

5. The apparatus of claim 3, wherein the reagent material is prothrombin.

6. The apparatus of claim 3, wherein the electrodeposited metal is nickel.

7. A method to detect the presence of a target compound, the method comprising:
    providing a thin film optical interference apparatus, the apparatus comprising a single layer of an anodizable metal, the layer having a first portion that is anodized to form a porous metal oxide and a second portion that is non-anodized underlying the first portion, wherein the first portion of the layer comprises a first thickness and a first refractive index generating a first optical path length, and the second portion of the layer comprises a second thickness and a second refractive index generating a second optical path length that is different from the first optical path length providing a first interference colour, and a non-anodized metal electrodeposited on the porous metal oxide providing an enhanced interference colour compared to the first interference colour,
    contacting the surface of the apparatus with a sample for the target compound;
    detecting the presence of the target compound upon binding of the target compound to the apparatus wherein a third thickness and a third refractive index generates a third optical path length different from the first and second optical path lengths, resulting in a detectable change in interference colour indicative of the presence of the target compound.

8. The method of claim 7, wherein the single layer of the anodizable metal comprises aluminum or an aluminum-based alloy.

9. The method of claim 8, wherein the apparatus further includes a reagent material on the porous metal oxide, the reagent material being capable of binding to the target compound, and providing a second interference colour different from the first interference colour, and wherein the electrodeposited metal provides an enhanced interference colour compared to the second interference colour.

10. The method of claim 9, wherein the target compound is a member of a binding pair selected from the group consisting of an antigen-antibody, an aptamer-antigen, a protein-protein, a toxin-receptor, an enzyme-receptor and an enzyme-substrate.

11. The method of claim 9, wherein the sample is a biological fluid selected from the group consisting of blood, urine, saliva, and tissue.

12. The method of claim 9, wherein the target compound binds with the reagent material to form a complex.

13. The method of claim 9, wherein the electrodeposited metal is selected from the group consisting of nickel, molybdenum, and copper.

14. The method of claim 9, wherein the reagent material is prothrombin.

15. The method of claim 9, wherein the electrodeposited metal is nickel.

16. A method of manufacturing a thin film optical interference apparatus for detecting the presence of a target compound, the method comprising:
    providing a single layer of an anodizable metal,
    anodizing the single layer of the anodizable metal to form a first portion that is anodized to provide a porous metal oxide, and a second portion that is non-anodized underlying the first portion, wherein
    the first portion of the layer comprises a first thickness and a first refractive index generating a first optical path length,
    the second portion of the layer comprises a second thickness and a second refractive index generating a second optical path length, wherein the second optical path length is different than the first optical path length providing a first interference colour, and
    electrodepositing a non-anodized metal onto the single layer of the anodizable metal providing an enhanced interference colour compared to the first interference colour,
    wherein upon binding of the target compound to the apparatus, a third thickness and a third refractive index generates a third optical path length, the third optical path length being different than the first and second optical path lengths, resulting in a detectable change in interference colour indicative of the presence of the target compound.

17. The method of claim 16, wherein the single layer of the anodizable metal is aluminum or an aluminum-based alloy.

18. The method of claim 17, further comprising providing a reagent material on the porous metal oxide, the reagent material being capable of binding to the target compound, and providing a second interference colour different from the first interference colour, and wherein the electrodeposited metal provides an enhanced interference colour compared to the second interference colour.

19. The method of claim 18, wherein the reagent material is prothrombin.

20. The method of claim 18, wherein anodizing the single layer of the anodizable metal comprises anodically polarizing the metal in an electrolytic cell selected from the group consisting of phosphoric acid, oxalic acid, sulfuric acid, and combinations thereof.

21. The method of claim 18, wherein anodizing the single layer of the anodizable metal is carried out at a voltage of up to 150V.

22. The method of claim 18, wherein the electrodeposited metal is selected from the group consisting of nickel, molybdenum, and copper.

23. The method of claim 18, wherein the electrodeposited metal is nickel.

24. The method of claim 23, wherein the method comprises anodizing before or after the electrodeposition of the non-anodized metal.

* * * * *